United States Patent [19]

Clarkson et al.

[11] Patent Number: 5,023,267
[45] Date of Patent: Jun. 11, 1991

[54] MICROBIOLOGICAL CONTROL AGENT

[75] Inventors: Douglas Clarkson, Aughton; Richard P. Clifford, South Wirral; Alan Marshall, Warrington, all of England

[73] Assignee: W. R. Grace & Co.-Conn., New York, N.Y.

[21] Appl. No.: 353,133

[22] Filed: May 17, 1989

Related U.S. Application Data

[62] Division of Ser. No. 153,286, Feb. 8, 1988, Pat. No. 4,863,616.

[30] Foreign Application Priority Data

Feb. 25, 1987 [GB] United Kingdom ............. 8704416

[51] Int. Cl.$^5$ .................. A01N 43/80; C09D 5/16
[52] U.S. Cl. .................. 514/372; 514/516; 514/937; 514/975; 106/18.33
[58] Field of Search .......... 514/372, 516, 937, 978; 106/18.33

[56] References Cited

U.S. PATENT DOCUMENTS

| | | | |
|---|---|---|---|
| 3,790,677 | 2/1974 | Bader et al. | 514/441 |
| 3,996,378 | 12/1976 | Payton | 514/516 |
| 4,069,341 | 1/1978 | Pierce | 514/516 |
| 4,188,376 | 2/1980 | Payne et al. | 514/373 |
| 4,289,581 | 9/1981 | Katayama et al. | 162/161 |
| 4,334,957 | 6/1982 | Katayama et al. | 162/161 |
| 4,379,137 | 4/1983 | Ehlers et al. | 424/78 |
| 4,454,146 | 6/1984 | Borovian | 514/372 |
| 4,466,975 | 8/1984 | Magami et al. | 514/373 |
| 4,518,610 | 5/1985 | Umekawa et al. | 514/516 |
| 4,601,831 | 7/1986 | Cook | 210/692 |
| 4,616,037 | 10/1986 | LeMarre et al. | 514/515 |
| 4,863,616 | 9/1989 | Clarkson et al. | 210/755 |

FOREIGN PATENT DOCUMENTS

| | | |
|---|---|---|
| 0209260 | 1/1987 | European Pat. Off. |
| 3201761 | 9/1983 | Fed. Rep. of Germany |
| 2296623 | 7/1976 | France |
| 1519329 | 7/1978 | United Kingdom |
| 2022416 | 12/1979 | United Kingdom |
| 2092446 | 8/1982 | United Kingdom |
| 2098067 | 11/1982 | United Kingdom |
| 2138799 | 10/1984 | United Kingdom |

OTHER PUBLICATIONS

Chemical Abstracts (vol. 101): 7142k.
5/77 Japanese Patent Reports, Chemical, vol. 77, No. 16, p. 3.
1973 Chemical Abstracts, vol. 79, p. 160.
1976 Chemical Abstracts, vol. 84, pp. 171, 379, 505.
1977 Chemical Abstracts, vol. 86, pp. 150, 297.
1980 Chemical Abstracts, vol. 92, pp. 358, 428.
1980 Chemical Abstracts, vol. 93, p. 732.
1981 Chemical Abstracts, vol. 94, p. 202.
1981 Chemical Abstracts, vol. 95, pp. 223, 226.
1982 Chemical Abstracts, vol. 96, pp. 194, 238.
1982 Chemical Abstracts, vol. 97, pp. 187, 257, 331.
1983 Chemical Abstracts, vol. 98, p. 195.
1984 Chemical Abstracts, vol. 101, p. 611.
1985 Chemical Abstracts, vol. 102, pp. 222, 223, 338.
1985 Chemical Abstracts, vol. 103, p. 514.
1986 Chemical Abstracts, vol. 104, pp. 243, 265, Res. Disclosure 22520.
Industrial Microbicides Brochure; N-octyl-isothiazolones.

Primary Examiner—Frederick E. Waddell
Assistant Examiner—Kevin Weddington
Attorney, Agent, or Firm—James P. Barr

[57] ABSTRACT

A method of treating an aqueous or non-aqueous system, including paints and adhesives, is described which comprises adding to the system a thiolan of the formula:

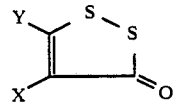

wherein each of X and Y, which may be the same or different, represents fluorine, chlorine or bromine, in combination with an alkylene bisthiocyanate and a 2-N-alkyl-4-isothiazolin-3-one.

16 Claims, No Drawings

MICROBIOLOGICAL CONTROL AGENT

This is a division of application Ser. No. 153,286, filed Feb. 8, 1988, now U.S. Pat. No. 4,863,616.

This invention relates to the treatment of aqueous systems, especially cooling water systems and water systems used in paper pulping and manufacture, as well as non-aqueous systems which can be termed functional fluids.

In industrial cooling water systems, for instance in industrial cooling towers, the water used is not, of course, sterile with the result that bacteria accumulate in the system and this quite commonly gives rise to a slimy deposit on the surfaces of the system which come into direct contact with the cooling water. A similar situation applies in paper making; slime can deposit on any of the surfaces with which the water comes into contact including the paper pulping bath, on the paper web and in the recirculating back pipework. Again such problems arise in the extraction and refining of sugar.

A large variety of different microbiological control agents have been used for the purpose of killing these bacteria and/or inhibiting slime formation or for dispersing and killing microbiological slime. There is also a need for fungicidal agents. Some of the most effective fungicidal agents are organometallic compounds, in particular tributyl tin compounds. Unfortunately although such compounds are effective fungicidal agents they are toxic so that they are environmentally unacceptable. Accordingly there is a need for a broad spectrum microbiological control agent which is environmentally acceptable.

There has been proposed the use of a combination of 5-oxo-3,4-dichloro-1,2-dithiolan (or 4,5-dichloro-1,2-dithiol-3-one) which has the formula:

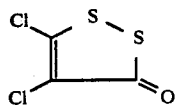

and methylene bisthiocyanate; although there is a synergistic effect between these two biocides the combination does not have broad spectrum control. The problem is to provide a formulation which makes use of this synergistic effect while being environmentally acceptable. It has surprisingly been found that certain isothiazolinones are not only compatible with the dithiolan and the isocyanate but also do not adversely affect the synergism between them while providing the formulation with broad spectrum activity without being toxic.

Accordingly the present invention provides a method of treating an aqueous or non-aqueous system which comprises adding to the system a thiolan of the formula:

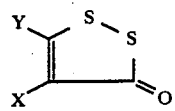

wherein each of X and Y, which may be the same or different represents fluorine, chlorine or bromine, an alkylenebisthiocyanate and a 2-N-alkyl-4-isothiazolin-3-one.

The first component is preferably one in which X and Y represent chlorine i.e. 4,5-dichloro-1,2-dithiol-3-one.

This compound is known from, for example, Japanese Patent Publication No. 14294/1977. It can be prepared by, for example, heating 1,1,2,3,3,3-hexachloroprop-1-ene, or the intermediate 2,3,3-trichloro-propenoic acid, with sulphur and steam (see, for example, DE-A-3201761). The other compounds can be prepared similarly from the corresponding 2,3,3-trihalo-propenoic acids.

The second component added to the system is an alkylenebisthiocyanate. The preferred thiocyanate used are ethylenebisthiocyanate and methylenebisthiocyanate which is especially preferred.

The 2-N-alkyl-4-isothiazolin-3-one is preferably one in which the alkyl group contains 2 to 10 carbon atoms, especially 8 carbon atoms; this latter compound is available commercially as Kathan 893 from Rohm and Haas.

Although it will normally be more convenient to add the components as a single mixture it is, of course, possible to add them severally or separately. In such circumstances the thiolan is suitably added as a solution in a solvent, optionally together with the thiocyanate; the thiazolinone will, in general, be a liquid which can be added direct; for ease of control they are added as a dilute solution in an appropriate solvent. The present invention also provides a composition suitable for addition to an aqueous or non-aqueous system which comprises at least one thiolan as defined above, at least one alkylenebisthiocyanate and at least one 2-N-alkyl-4-isothiazolin-3-one.

The present invention finds utility in a variety of aqueous and non-aqueous systems. Aqueous systems to which the present invention may be applied include those used in the extraction and refining of sugars, in the textile industry, in finishing agents and conditioners, in aqueous functional fluids and in aqueous e.g. emulsion paints but, more particularly, in the paper making industry and in cooling water systems. Among non-aqueous systems there may be mentioned non-aqueous functional fluids and oils, for example cutting oils and heavy oil sludges as well as in paint systems, for example protective paints for marine use. Typically a paint of the present invention comprises, apart from the three microbiological components, a polymer, one or more pigments or colouring agents together with an oil or water base and, optionally, one or more dispersants and defoamers. Suitable polymers include acrylic polymers and vinyl polymers, for example vinyl acetate and vinyl chloride polymers, specifically a copolymer of vinyl acetate, ethylene and vinyl chloride. The combination also finds utility in the preservation of water-based and non-aqueous adhesives, for example those based on casein, gelatine, starch, cellulose and vegetable glues. The compositions are effective against both fungal and bacterial contaminants of such systems.

In paper-making, the active ingredients may be added to the paper pulping bath, the recirculating back-water, or, for example, to a holding tank containing generally moist, pulp or along with one or more chemical additives used in paper-making or containing starch or paper coating masses. Such additives include starch, for example, potato or corn starch, titanium dioxide, a defoamer such as fatty acid alcohol, a size for example a rosin size based on abietic acid, a neutral size based on alkyl ketene dimer or a succinic acid anhydride based on size, a wet strength resin such as, if neutral, an epichlorohydrin polyamide or, if acid, a melamine- or ureaformaldehyde resin, various polymers used as dispersans or retention aids such as polyacrylates, polymethacrylates, polyamides and polyacrylamides, clay, chalk, fillers such as carboxymethyl cellulose, polyvinyl alcohol and optical brightening agents. The invention also finds utility in systems used to treat a pre-formed paper web, for example finishing agents, such as those used to give the paper a gloss finish.

In cooling water systems, the active ingredients may be introduced at any location where they will be quickly and efficiently mixed with the water of the system although it will generally be most convenient to add them to the make-up or feed water lines through which the water enters the system. Typically, an injector calibrated to deliver a pre-determined amount periodically or continuously to the make-up water is employed. Of course, conventional water treatment additives such as corrosion inhibitors and lignin derivatives can also be included.

If the thiolan and thiocyanate are added as a composition, the total concentration of the active ingredients will, in general, be from 0.1 to 20% by weight, preferably from 2 to 8% by weight. In general the weight ratio of the thiolan to the thiocyanate will be from 1:10 to 10:1, preferably from 1:5 to 5:1, especially from 1:2 to 2:1, while the weight ratio of each of the dithiolan and the thiocyanate to isothiazolinone will be from 1:1 to 20:1, preferably 1:1 to 5:1, especially from 1:1 to 2:1. A particularly preferred weight ratio of dithiolan:thiocyanate:isothiazolinone is about 1.25:1.25:1. Clearly, if the ingredients are added separately the same relative concentrations apply.

The amount of the combination (active ingredient) added to the system will normally be from 0.1 to 40 ppm, preferably from 0.4 to 40 ppm. The concentration of biocides will, of course, vary depending on the nature of the biocides and on the nature and amount of the bacteria present but, clearly, an amount effective to control the bacteria present should be used.

The active ingredients are suitably formulated as a liquid composition but they may also be used in the form of, say, a powder.

The solvents used in the liquid preparation are preferably organic solvents and especially substantially anhydrous organic solvents because 4,5-dichloro-1,2-dithiol-3-one tends to hydrolyse in the presence of water. Preferably hydrophilic solvents which can dissolve the active ingredients, are miscible with water and can give storable, stable compositions are used unless, of course, the composition is to be added to, say, a cutting fluid in which an oil-soluble solvent such as a hydrocarbon solvent is generally used. Examples of suitable hydrophilic solvents include glycols, such as ethylene glycol, propylene glycol, diethylene glycol and dipropylene glycol; glycol ethers, such as 2-methyoxyethanol, 2-ethoxyethanol, 2-phenoxyethanol, diethylene glycol monomethyl ether, propylene glycol monomethyl ether, dipropylene glycol monomethyl ether and tripropylene glycol monomethyl ether; and alcohols containing up to 8 carbon atoms. Mixtures of two or more solvents may also be used. Butyl diglycol and polyethylene glycols are particularly preferred, for example, those having a molecular weight of 190 to 210; also preferred are 2-butoxyethanol, propylene glycol, polypropylene glycols and diethylene glycol.

The composition may also contain one or more dispersing agents. Examples or suitable dispersing agents include cationic, anionic, non-ionic or amphoteric surfactants; non-ionic surfactants are preferred. Typical surfactants which can be used include ethylene oxide adducts, especially ethoxylated phenols having the general formula:

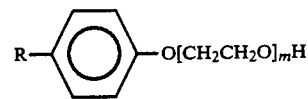

where m represents 2 to 40 and R represents $C_n H_{2n+1}$ in which n is from 0 to 18, as well as alkylamine-polyoxypropylene-polyoxyethylene adducts and alkylolamides.

Preferred ethoxylates are those derived from phenol itself, nonyl phenol and dodecyl phenol and those containing 4 to 15 ethoxylate groupings. Especially preferred is "Ethylan HB4" which is a phenol ethoxylate containing about 4 ethoxylate units.

Typical alkylamine polyoxypropylene polyoxyethylene adducts include N,N,N',N'-polyoxyethylene-polyoxypropylene-ethylenediamine block copolymers, for example those having the formula:

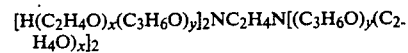

in which each x and each y has a value which can differ from one block to the next. These materials are available commercially as "Tetronics", varying in molecular weight and the relative proportion of ethylene oxide and propylene oxide units; in general the ethylene oxide units represent 10 to 80% by weight of the product while propylene units provide a molecular weight of, say, 2,000 to 25,000.

Typical alkylolamides which can be used include those obtained from a fatty acid containing, say, 8 to 18 carbon atoms, for example coconut fatty acids, and an alkanolamine, preferably ethanolamine or diethanolamine. Some such materials are available commercially under the trade mark Concensate.

Typically the ratio of dispersant to biocide will be from 1:20 to 200:1, preferably from 1:1.6 to 1.25:1.

The following Examples further illustrate the present invention. In these Examples active ingredient (I) is 5-oxo-3,4-dichloro-1,2-dithiolan, active ingredient (II) is methylene bisthiocyanate and active ingredient (III) is 2-N-octyl-4-isothiazolin-3-one. Formulation A has the following formulation:

| Active Ingredient | (I) | 1.25% | (40% Concentration) |
|---|---|---|---|
| Active Ingredient | (II) | 0.5% | |
| Active Ingredient | (III) | 1.0% | (45% Concentration) |
| Diethylene glycol | | 87.25% | |

This product, irrespective of the chosen solvent, is stable between −4° C. and 45° C. and is readily water miscible at normal use concentrations. As shown below, this formulation when evaluated by comparison with (Formulation B) containing the active ingredients methylene bisthiocyanate (1%), 50% glutaraldehyde (10%) and tributyl tin chloride (1.25%), demonstrated superior activity against *Pseudomonas fluorescens, Legionella pneumophila, Aspergillus niger*, Penicillium sp and *Desulphoribrio desulphuricans*.

EXAMPLE 1

Formulation A was added to a cell suspension of the bacterial species *Pseudomonas fluorescens* at concentrations of 50, 100 and 200 ppm. The pH of the suspension was 7.0 and its temperature was 22° C. Formulation B was similarly evaluated.

The results tabulated below are expressed in terms of percentage survival of bacterial cells following exposure to the biocide for 1, 2 and 4 hours.

| Biocide Contact | | Biocide Concentration (ppm) | | |
|---|---|---|---|---|
| Period (Hrs) | Biocide | 50 | 100 | 200 |
| 1.0 | A | 21.0 | 2.0 | 0.01 |
|  | B | 65.0 | 68.0 | 65.0 |
| 2.0 | A | 0.1 | 0.01 | 0.001 |
|  | B | 25.0 | 21.0 | 8.0 |
| 4.0 | A | 0.01 | 0.001 | 0.001 |
|  | B | 0.15 | 0.025 | 0.01 |

EXAMPLE 2

Formulation A was added to a cell suspension of the bacterial species *Legionella pneumophila* at concentrations of 25, 100 and 200 ppm. The pH of the suspension was 7.0 and its temperature was 22° C. Formulation B was similarly evaluated.

The results tabulated below are expressed in terms of percentage survival of bacterial cells following exposure to the biocide for 1, 2 and 4 hours.

| Biocide Contact | | Biocide Concentration (ppm) | | |
|---|---|---|---|---|
| Period (Hrs) | Biocide | 25 | 100 | 200 |
| 1.0 | A | 35.7 | Nil | Nil |
|  | B | 73.6 | 63.2 | 0.1 |
| 2.0 | A | Nil | Nil | Nil |
|  | B | 52.6 | 52.6 | Nil |
| 4.0 | A | Nil | Nil | Nil |
|  | B | 10.0 | 0.1 | 0.1 |

EXAMPLE 3

Formulation A was added to a spore suspension of the fungal species *Aspergillus niger* at concentrations of 50, 100 and 200 ppm. The pH of the suspension was 7.0 and its temperature was 22° C. Formulation B was similarly evaluated.

The results tabulated below are expressed in terms of percentage survival of fungal spores following exposure to the biocide for 1, 2 and 4 hours.

| Biocide Contact | | Biocide Concentration (ppm) | | |
|---|---|---|---|---|
| Period (Hrs) | Biocide | 50 | 100 | 200 |
| 1.0 | A | 28.0 | 10.0 | 0.01 |
|  | B | 95.0 | 90.0 | 90.0 |
| 2.0 | A | 17.0 | 6.5 | 0.01 |
|  | B | 85.0 | 70.0 | 49.0 |
| 4.0 | A | 16.0 | 1.0 | Nil |
|  | B | 84.0 | 78.0 | 18.0 |

EXAMPLE 4

Formulation A was added to a suspension of fungal spores of Penicillium sp at concentrations of 50, 100 and 200 ppm. The pH of the suspension was 7.5 and its temperature was 22° C. Formulation B was similarly evaluated.

The results tabulated below are expressed in terms of percentage survival of fungal spores following exposure to the biocide for 1, 2 and 4 hours.

| Biocide Contact | | Biocide Concentration (ppm) | | |
|---|---|---|---|---|
| Period (Hrs) | Biocide | 50 | 100 | 200 |
| 1.0 | A | 33.3 | 16.6 | 14.1 |
|  | B | 77.7 | 71.1 | 66.5 |
| 2.0 | A | 20.0 | 14.3 | 8.2 |
|  | B | 42.8 | 30.6 | 12.2 |
| 4.0 | A | 14.2 | 24.5 | 1.8 |
|  | B | 38.7 | 18.4 | 11.4 |

EXAMPLE 5

Formulation A was added to a cell suspension of the bacterial species *Desulphovibrio desulphuricans* at concentrations of 25, 50, 100 and 200 ppm. The pH of the suspension was 6.0 and its temperature was 22° C. Formulation B was similarly evaluated.

The results tabulated below are expressed in terms of percentage survival of bacterial cells following exposure to the biocide for 1, 2 and 4 hours.

| Biocide Contact | | Biocide Concentration (ppm) | | | |
|---|---|---|---|---|---|
| Period (Hrs) | Biocide | 25 | 50 | 100 | 200 |
| 1.0 | A | 14.0 | 10.0 | 0.01 | 0.01 |
|  | B | 67.5 | 19.0 | 0.01 | 0.01 |
| 2.0 | A | 3.4 | 2.4 | 1.5 | 0.01 |
|  | B | 21.0 | 7.8 | 0.01 | 0.01 |
| 4.0 | A | 43.75 | 11.7 | 1.3 | 0.01 |
|  | B | 33.3 | 1.25 | 0.01 | 0.01 |

We claim:

1. A composition suitable for addition to an aqueous or non-aqueous system which comprises a bactericidally effective amount of a thiolan of the formula

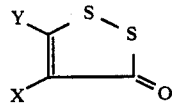

wherein each of X and Y, which may be the same or different, represents fluorine, chlorine, or bromine, an alkylenebis-thiocyanate and a 2-N-alkyl-4-isothiazolin-3-one wherein the weight ratio of thiolin to thiocyanate is from 1:10 to 10:1 and the weight ratio of thiolan or thiocyanate to isothiazolinone is from 1:1 to 20:1.

2. A composition according to claim 1 in which the thiolan is 5-oxy-3,4-dichloro-1,2-dithiolan.

3. A composition according to claim 1 in which the alkylene bisthiocyanate is methylene bisthiocyanate.

4. A composition according to claim 1 in which the isothiazolinone is 2-N-octyl-4-isothiazolin-3-one.

5. A composition according to claim 1 in which the weight ratio of thiolan to thiocyanate is from 1:2 to 2:1.

6. A composition according to claim 1 in which the weight ratio of thiolan or thiocyanate to isothiazolinone is from 1:1 to 2:1.

7. A composition according to claim 1 in which the weight ratio of thiolan:thiocyanate:isothiazolinone is about 1.25:1.25:1.

8. A composition according to claim 1 which contains a total of from 0.1 to 20% by weight of the active ingredients.

9. A composition according to claim 8 which contains a total of from 2 to 8% by weight of the active ingredients.

10. A composition according to claim 1 which is in the form of a solution in a hydrophilic organic solvent.

11. A composition according to claim 10 in which the solvent is butyl diglycol, a polyethylene glycol, 2-butoxy ethanol, propylene glycol, a polypropylene glycol or diethylene glycol.

12. A composition according to claim 1 which also contains a dispersing agent.

13. A composition according to claim 12 in which the dispersing agent is an ethoxylated phenol having the general formula:

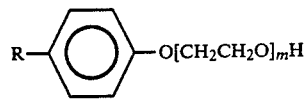

where m represents 2 to 40 and R represents $C_nH_{2n+1}$ in which n is from 0 to 18.

14. A composition according to claim 1 in which the ratio of dispersing agent to active ingredient is from 1:1.6 to 1.25:1.

15. A paint which comprises a thiolan as defined in claim 1, an alkylene bis-thiocyanate and a 2-N-alkyl-4-isothiazolin-3-one in an amount effective to control bacteria.

16. An adhesive which comprises a thiolan as defined in claim 1, an alkylene bis-thiocyanate and a 2-N-alkyl-4-isothiazolin-3-one in an amount effective to control bacteria.

* * * * *